United States Patent [19]

Sadjadi

[11] Patent Number: 5,383,018
[45] Date of Patent: Jan. 17, 1995

[54] APPARATUS AND METHOD FOR CALIBRATION OF PATTERNED WAFER SCANNERS

[75] Inventor: S. M. Reza Sadjadi, San Jose, Calif.

[73] Assignee: National Semiconductor Corporation, Santa Clara, Calif.

[21] Appl. No.: 997,226

[22] Filed: Dec. 28, 1992

[51] Int. Cl.$^6$ .................. G01J 1/02; G01N 21/88
[52] U.S. Cl. .................. 356/243; 356/237; 356/394
[58] Field of Search .......... 356/243, 237, 394, 338, 356/30, 371, 445, 446; 250/252.1 A, 562, 563, 572

[56] References Cited

U.S. PATENT DOCUMENTS

| | | | |
|---|---|---|---|
| 3,963,354 | 6/1976 | Feldman et al. | 250/572 |
| 4,378,159 | 3/1983 | Galbraith | 356/237 |
| 4,386,850 | 6/1983 | Leahy | 356/237 |
| 4,512,659 | 4/1985 | Galbraith et al. | 356/237 |
| 5,198,869 | 3/1993 | Monteverde et al. | 356/243 |
| 5,214,486 | 5/1993 | DeWitt | 356/243 |

Primary Examiner—Richard A. Rosenberger
Assistant Examiner—Hoa Q. Pham
Attorney, Agent, or Firm—Limbach & Limbach

[57] ABSTRACT

A calibration wafer for a patterned wafer scanner is constructed from a substrate of semiconductor material, typically silicon, in which a pattern of features has been etched into the periphery of each die by means of photolithographic techniques. Next, a layer or layers of films composed of materials which are typically used during the fabrication of integrated circuits are deposited. Then a substantially uniform distribution of particles of a known material and size distribution is deposited onto the wafer. A second embodiment of the calibration wafer is one in which a layer or layers of film are first deposited onto a substrate. Then a pattern of features is etched into the periphery of the film covering each die by means of photolithographic techniques. After this step, a substantially uniform distribution of particles is deposited. A method of using such a calibration wafer to calibrate a patterned wafer scanner is also disclosed.

12 Claims, 7 Drawing Sheets

APPARATUS AND METHOD FOR CALIBRATION OF PATTERNED WAFER SCANNERS

TECHNICAL FIELD

The present invention is generally directed to scanners used to detect defects on processed wafers of semiconductor material during the fabrication of semiconductor devices, and more specifically, to an apparatus and method for calibrating such scanners.

BACKGROUND OF THE INVENTION

Integrated circuits are produced by means of a fabrication process which converts a circuit design into an operable semiconductor device. The fabrication process consists of a sequence of steps which transforms a wafer of semiconductor material, typically silicon, into a device or devices with multiple layers, with each layer having a specific pattern of structures and interconnections.

After a wafer layer is patterned, samples are inspected to determine the number and location of surface defects acquired during fabrication, and to collect data for the purpose of evaluating the process control procedures used during that stage of the fabrication process. Defects are typically due to the deposition of particulate contaminants during the fabrication process, although they may also be due to the creation of surface irregularities. The inspection is usually carried out by a device known as a scanner. At the present time, there are three types of patterned wafer scanners in normal use.

The first type of scanner is a laser based scanner which uses a laser to scan the surface of a wafer. The scanner detects defects based on the magnitude of the light reflected or scattered after encountering the wafer surface. If a defect is not encountered by the light, the intensity of the scattered and reflected laser light is primarily within the level set by the background noise. However, if a defect is encountered, the scattered laser light produces a strong scattered light pulse, so that its intensity distribution differs from what would be detected in the absence of a defect.

Because the amount of light scattered and reflected from a wafer depends on whether a defect is present, defects can be detected by measuring the intensity of the scattered laser radiation. Signals with an intensity above the background noise level are assumed to correspond to defects.

The scattered laser light is detected by a photo multiplier tube which amplifies the electrical signal corresponding to the detected photons. A properly programmed computer can be used to store the location and intensity of the scattered light as a means of determining the location and estimated size of the defect (based on the scattering cross section). This data can also be used to determine the type of defect present on the wafer, based on polarization studies, estimates of the refractive index of particular materials, etc.

A second type of patterned wafer scanner detects defects by means of digital imaging. In this type of scanner, a digital image of a portion of a wafer is constructed and stored in memory. Another portion of the wafer, which is supposed to have the same pattern(s) is then scanned, and the two images are compared by a computer. If any differences are detected between the images, it is taken as an indication that a defect is present. Another way this type of scanner can be used is to construct a digital image of the same region of two different wafers. Comparison of the images can be used to detect random (as opposed to systematic) errors which occur during the fabrication process.

A third type of patterned wafer scanner detects defects by constructing a holographic image of the wafer surface. This technique is based on spatial frequency filtering which is performed in the Fourier Transform plane of the wafer pattern. Because the spatial frequency spectrum of most patterned wafers is distinct from the spatial frequency spectrum of defects, this method is very effective at separating the transform of a repetitive pattern of a device element (or unit cell) from that of a defect.

In order to apply this technique, a spatial frequency filter is generated and placed in the Fourier Transform plane to separate and remove the repetitive unit cell information from the defect information. The wavefront of the filtered spectrum, containing only the defect information, is then recorded in a hologram. Reconstruction of the recorded wave front from the hologram enables restoration of the filtered (defect) spectrum and permits its reverse ray tracing through the same lens used to perform the transform. The result is a high resolution image of the defects contained in the wafer. The locations and sizes of the defects are determined by scanning the image field with a solid-state light sensor. The defect data is then processed and made available to the engineers involved in the fabrication process.

A problem with the types of scanners discussed above is that if the wafer surface itself is textured or colored (such as occurs with metal or polysilicon materials), these features may be falsely detected as defects. To prevent such false detections, the sensitivity of the scanner is sometimes reduced. To make this masking of false defects consistent between wafers, the sensitivity adjustment must be performed repeatedly. This adds time to the fabrication process and introduces another variable which can affect comparisons of the number and types of defects detected on different wafers.

The sensitivity of a scanner can also be a function of the optics, or of the stability of the laser used in a particular scanner. This makes it even more difficult to compare defect data obtained from different wafers, or during different stages of the fabrication process.

A further difficulty is that because the operation of each of the types of scanners is based on different principles, their sensitivity may be a function of the type of defects present. For instance, some types of scanners are better at detecting high-contrast defects, while others are most sensitive to defects having a minimum size in a preferred dimension. This makes it even harder to compare scan results obtained from different stages of the fabrication process or between different types of scanners.

As indicated, patterned wafer scanners are an integral part of the quality control stage of semiconductor device fabrication. Therefore, it is important that there be no significant variation in their operation over time. This is one motivation for the development of a method of calibrating such scanners. In addition, because the sensitivity of the scanners varies as a function of the type and number of material layers deposited on a wafer and the type of defects present, correctly detecting defects during the entire fabrication process requires that the scanners be able to be calibrated at various stages of the process.

For example, during the deposition of the first few layers in a fabrication process, the scanners operate at their highest level of sensitivity. This is because there is not yet a sufficient number of background layers or structures to interfere with the detection capability of the scanner. As the number of material layers deposited increases, the background noise level increases and the scanner is less effective at detecting defects. As a result, a greater (and unrepresentative) proportion of the defects detected would be those occurring during the early stages of the fabrication process. This is actually contrary to what would be expected, since the level of defects is expected to increase as the wafer is processed.

Another benefit of having a reliable calibration scheme for patterned wafer scanners is that it would permit the direct comparison of the performance of different scanners. This would assist vendors of such scanners to market them to potential customers, because the detection capability of a scanner when applied to a particular stage or type of fabrication process could be determined based on a standardized scale.

At present, calibration methods do exist for unpatterned wafer scanners, that is scanners which examine silicon wafers which have been cleaned and polished, but have not yet had material layers deposited or structures formed on them. These methods are usually based on the use of a calibration wafer which is formed by depositing particles (such as polystyrene latex, referred to as PSL) on unprocessed wafers. However, this approach is not suitable for use with patterned wafer scanners for several reasons.

The first reason is that patterned wafer scanners utilize a pattern recognition technique for scanning over the wafer. The lack of a pattern on the wafer makes it difficult (if not impossible) for the scanners to consistently go to the same location on a wafer when different wafers are scanned.

In addition, the patterns on a wafer are used for adjusting the focus of the scanner. Improper or partial focusing can cause a reduction of the scanner's sensitivity. This can cause the results of the scan to be less useful and not reproducible.

Finally, the proper detection of defects using a patterned wafer scanner requires that highly repetitive patterns be used. This is because repetitive patterns produce the least amount of optical and electrical noise, thereby increasing the likelihood of obtaining meaningful scan results when the scanner is operated at high sensitivity levels.

A related reason for not using the same calibration standard as that used for unpatterned wafer scanners is that the deposition of PSL particles on an unpatterned wafer may not be a realistic representation of the type of defects introduced during an actual fabrication process. A more accurate calibration would be one based on a calibration wafer which more closely represented the types of materials and deposition techniques used during the fabrication of an actual device.

Attempts have been made to develop calibration wafers for patterned wafer scanners. Vendors of scanners have fabricated wafers with a known defect pattern using photolithographic techniques, and used these to calibrate their equipment. However, one problem with this method is that the sizes and shapes of the defects are limited by the resolution achieved by the photolithographic techniques. At present the resolution of such techniques places a lower limit of 0.5 $\mu m$ on the size of the features which can be transferred to a wafer. However, patterned wafer scanners are capable of detecting and resolving features as small as 0.1 $\mu m$. This means that defects which may be capable of impacting the operation of devices cannot be reproduced on calibration wafers. The result is that the defect data cannot be relied on to the extent desired. This problem points out the desirability of developing a non-lithography based method of creating defects on calibration wafers.

Another means of producing calibration wafers for patterned wafer scanners is based on ion beam etching. This involves using a focused ion beam to etch a desired pattern of features onto a wafer. This method is of limited utility because some types of scanners cannot adequately scan calibration wafers which contain this type of defect.

Although it is possible to use any wafer having a repetitive pattern and on which has been deposited particles of a known size and material (such as a wafer produced in the course of a normal fabrication process) as a calibration standard, this does not provide an optimal method for calibrating patterned wafer scanners. One reason is that in most cases, such wafers lack the amount of scanable area required to obtain statistically valid data.

Another problem is that while using such a wafer assists with determining the repeatability of the scan results for that type of wafer, it does not permit the sensitivity of the scanner to be evaluated. This is because of the difficulty in precisely controlling the concentration of deposited particles within small regions, so that the level of defects on the wafer would not be known to the desired degree of certainty. Such a calibration method would also not allow the capabilities of different scanners to readily be compared. Instead, a calibration method is needed which will enable the scan results from different scanners to be compared with each other, and which is suitable for assessing the sensitivity of such scanners.

What is desired is a uniform calibration wafer for patterned wafer scanners and a method for using such wafers. These should allow the defect detection capabilities of different scanners to be compared, and should be readily useable during the entire fabrication process.

SUMMARY OF THE INVENTION

The present invention is directed to an apparatus and method for calibrating patterned wafer scanners which are used to detect defects on wafers of semiconductor material during various stages of the semiconductor device fabrication process. A calibration wafer is constructed from a substrate of semiconductor material, typically silicon, into which has been etched or onto which has been formed a minimal pattern by means of photolithographic techniques. The pattern is one sufficient to permit the scanner to perform its detection, stepping, and focusing operations, where the detection capability is sufficient to provide statistically valid data.

Next, a layer or layers of films composed of materials which are typically used during the fabrication of integrated circuits are deposited. Then a substantially uniform distribution of particles of a known material and size distribution is deposited onto the wafer. The particles are of a type and size typical of those deposited or encountered during an integrated circuit fabrication process. The result is a calibration wafer which can be used to calibrate patterned wafer scanners.

A second embodiment of the calibration wafer of the present invention is one in which a layer or layers of film are first deposited onto a substrate. Then a minimal pattern is etched into the film using photolithographic techniques. After this step, a substantially uniform distribution of particles is deposited.

The present invention is also directed to a method of using such a calibration wafer to calibrate a patterned wafer scanner. The calibration method involves scanning a prepared calibration wafer with the scanner set to maximum sensitivity, or to the sensitivity setting used for previous scans, and comparing the results to the known distribution and types of defects placed on the calibration wafer. If the results are not sufficiently close to the defects known to exist on the calibration wafer, the scanner's sensitivity is adjusted and the scan and comparison steps are repeated.

Further objects and advantages of the present invention will become apparent from the following detailed description and accompanying drawings.

DESCRIPTION OF THE PREFERRED EMBODIMENT

Figure 1:
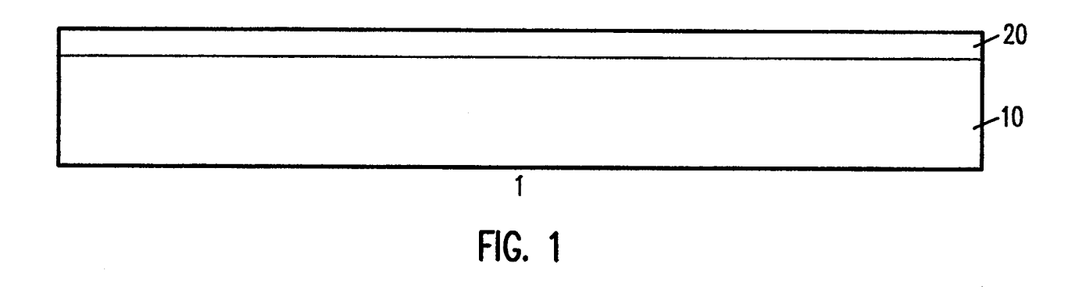
FIG. 1 is a cross-sectional view of an unpatterned wafer of semiconductor material which will be used to fabricate a calibration wafer according to a first embodiment of the present invention, and onto which has been deposited a layer of film.

Referring to the figures, and in particular to FIG. 1, there is shown a cross-sectional view of an unpatterned wafer of semiconductor material 10, typically silicon, which provides a basis for the fabrication of a calibration wafer 1 according to a first embodiment of the present invention. A layer of film 20 has been deposited onto wafer 10 by deposition techniques known in the semiconductor industry.

The layer of film 20 is preferably composed of one of the types of films deposited on wafers during the normal integrated circuit fabrication process, i.e., silicon oxide, silicon nitride, polysilicon, aluminum, tungsten, copper, or a type of silicide. If desired, several layers of such film may be deposited on wafer 10.

It is now desired to etch a pattern of shapes into the film layer(s). This is usually accomplished by means of standard photolithographic techniques, although other patterning techniques can be used. First, a layer of resist is spun onto the top surface of wafer 10. The resist is used in conjunction with a lithography mask and illumination source to define the desired pattern of shapes on film layer 20.

The resist layer is exposed using the mask and illumination source. The mask used should have sufficient closed area if a positive resist is used, or sufficient open area if a negative resist is used. The sufficiency of the open or closed area depends on the scanning tool which will be used, and on the desire to obtain statistically valid results when detecting defects. The patterns etched into film layer 20 should be on the periphery of the layer for each die which is formed from wafer 10 so as to leave the central portion available for the subsequent deposition of particles which are representative of defects.

An important point is that the scanning tools require a pattern in order to focus properly on the wafer and in order to proceed with the detection of defects. This means that a certain amount of the surface area of a calibration wafer should be occupied by a pattern. However, it is desirable to minimize the amount of area so occupied in order to have sufficient surface area on which to deposit particles representative of the types and numbers of defects which provide the basis for the calibration scan.

One way to quantify the amount of or limit to the area which should be occupied by the pattern is to consider what confidence level is desired regarding the number and type of detected defects. Typically, it is desired that there be a 95% confidence level that the observed number of defects is within some range of the actual (known) number of defects. The goal is then to determine the maximum amount of area which can be occupied by the patterns so as not to impact this desired degree of confidence.

If the observed number of defects is given by n, the actual number of defects is given by $n_a$, and it is desired that there be a 95% confidence level that n is within a fraction f of $n_a$, then this relationship can be represented as:

$$(1-f) < n/n_a < (1+f). \qquad (1)$$

This can be expressed as:

$$1/(1+f) < n_a/n < 1/(1-f). \qquad (2)$$

If we assume that the distribution of defects on a wafer can be modeled by a poisson distribution, then for n>50, the poisson distribution tends toward normality with a mean value of n and variance n. In this case a 95% confidence level for the observed number of defects n can be expressed as:

$$n - 2*n^{\frac{1}{2}} < n_a < n + 2*n^{\frac{1}{2}}. \qquad (3)$$

This relationship can be expressed as:

$$1 - 2*n^{-\frac{1}{2}} < n_a/n < 1 + 2*n^{-\frac{1}{2}}. \qquad (4)$$

Comparing equations (2) and (4), it can be concluded that a 95% confidence level with a variability of f constrains the observed number of defects n to fall within the following limits:

$$4*(1-f)^2/f^2 < n < 4*(1+f)^2/f^2. \quad (5)$$

If the area of the entire wafer is A and the area which is patterned is given by $A_p$, then if the particle density deposited on the wafer is N, the number of observed defects is given by:

$$n = N*(A - A_p). \quad (6)$$

If in order to be conservative, the upper limit of equation (5) is used for the number of observed defects, then combining equations (5) and (6) gives:

$$N*(A - A_p) \approx 4*(1+f)^2/f^2. \quad (7)$$

Rearranging equation (7) gives:

$$A_p/A = 1 - 4*(1+f)^2/N*A*f^2. \quad (8)$$

Equation (8) can then be used to determine the maximum fraction of the total surface area of the wafer which may be occupied by a pattern so as not to reduce the desired 95% confidence level in the observed number of defects, based on the values used for N, A, and f.

As an example, assume that it is desired that there be a 95% confidence level that the observed number of defects (n) falls within 2.5% (f=0.025) of the actual number of defects ($n_a$). If a circular wafer having a 6 inch diameter (A=182 cm$^2$) is used as the calibration wafer, and the concentration of deposited particles is 50 particles/cm$^2$ (N=50), then:

$$A_p/A = 1 - 4*(1+0.025)^2/50*182*0.025^2).$$

Carrying out the calculation gives the result:

$$A_p/A = 0.26.$$

Thus, in this case, it is desired that the pattern occupy at most 26% of the total surface area of the wafer. The previous analysis is meant to be an example of how the desired amount of patterned surface area can be determined. Other forms of statistical analysis may also be performed for the same purposes.

Continuing now with the details of how the calibration wafer is fabricated, after the resist is exposed, it is developed. This removes the resist in the exposed regions if positive resist is used, or leaves the resist in those regions if negative resist is used. Next the layer or layers of film 20 are etched. The depth of the etch should be such that the etched pattern is easily detectable by the scanning tool which is being used. The etch chemistry (wet, dry, etc.) chosen depends on the type of film, and its method of determination is well known in the semiconductor industry.

Figure 2:
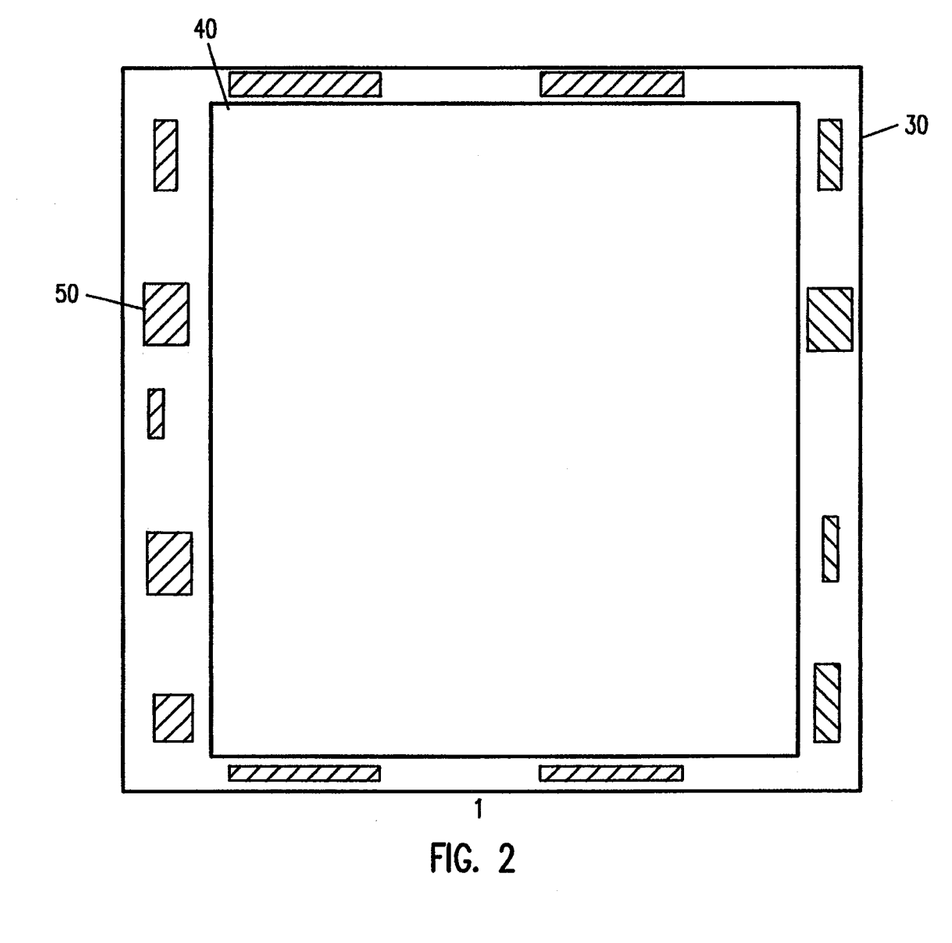
FIG. 2 is a top-view of a die on the wafer of FIG. 1, after the etching of a minimal pattern of features into the film layer by means of standard photolithographic techniques or other method of patterning the layer.

After the etching, the remaining resist is removed by known chemical or dry methods. At this point, the wafer 10 may be cleaned by chemical or mechanical methods if desired. As shown in FIG. 2, which is a top-view of a die 15 on wafer 1 of FIG. 1 after etching, the use of the mask to define the patterns on film layer 20 serves to divide the top surface of die 15 into a center region 40 which is devoid of any pattern, and a peripheral region 30 within which a pattern of shapes 50 is defined and etched into film layer 20.

Figure 3:
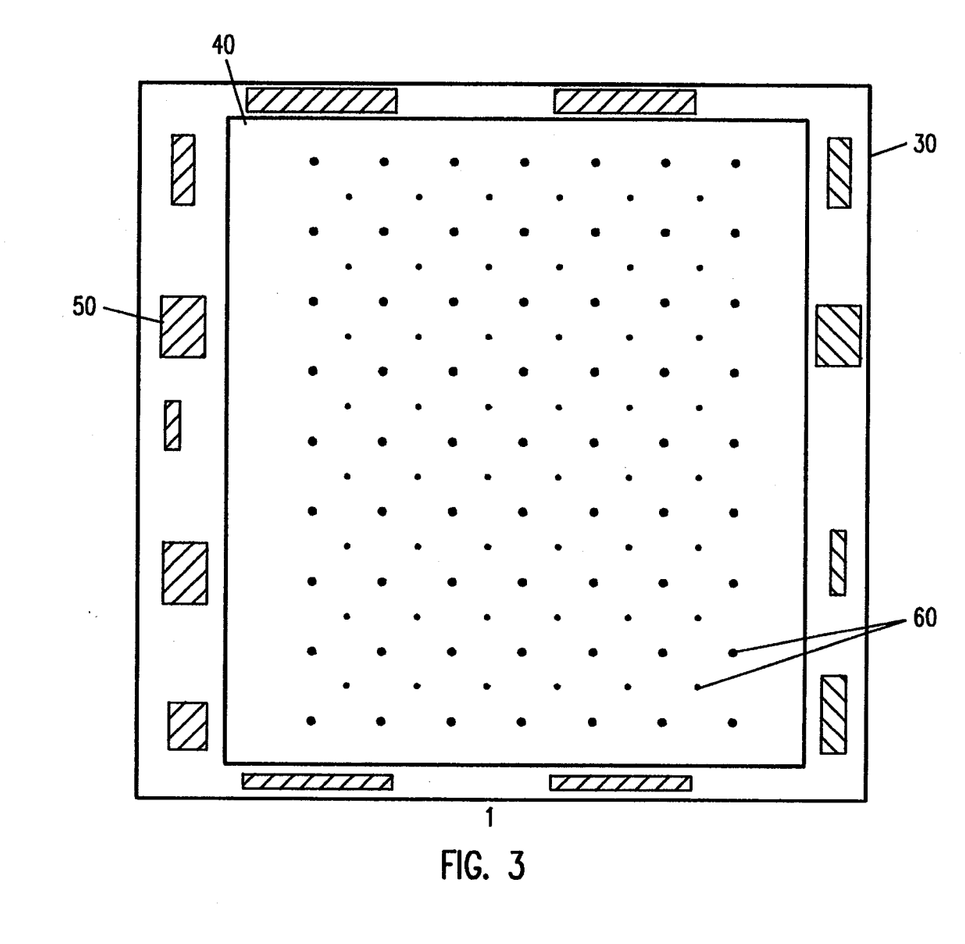
FIG. 3 is a top-view of the die of the wafer of FIG. 2 onto which has been deposited a substantially uniform distribution of particles of a type or types typically deposited during the fabrication of a semiconductor device.

The next step is to deposit a substantially uniform distribution of particles onto the surface of calibration wafer 1. As shown in FIG. 3, the particles 60 should be deposited within the central region 40 of die 15. The particles should be of a known size distribution and material. If desired, several deposition stages, corresponding to different types of particles, may be used. The particles can be composed of any material typically used in the integrated circuit fabrication process, i.e., silicon, silicon oxide, silicon nitride, polysilicon, etc. The deposition should be carried out in a controlled environment such as a clean room or other clean environment.

Calibration wafer 1 should then be tested against a primary calibration wafer (if one exists) for purposes of quality control. If desired, a set of calibration wafers 1 may be produced, each with a different film layer 20 and particle distribution 60. Each wafer so produced can be used to calibrate the scanner during a particular phase of a standard fabrication process. In this case, the type of film and type and number of particles deposited on the wafer depends on the stage of the fabrication process involved. The calibration wafer or wafers 1 should then be assembled and wrapped in a clean environment.

Figure 4:
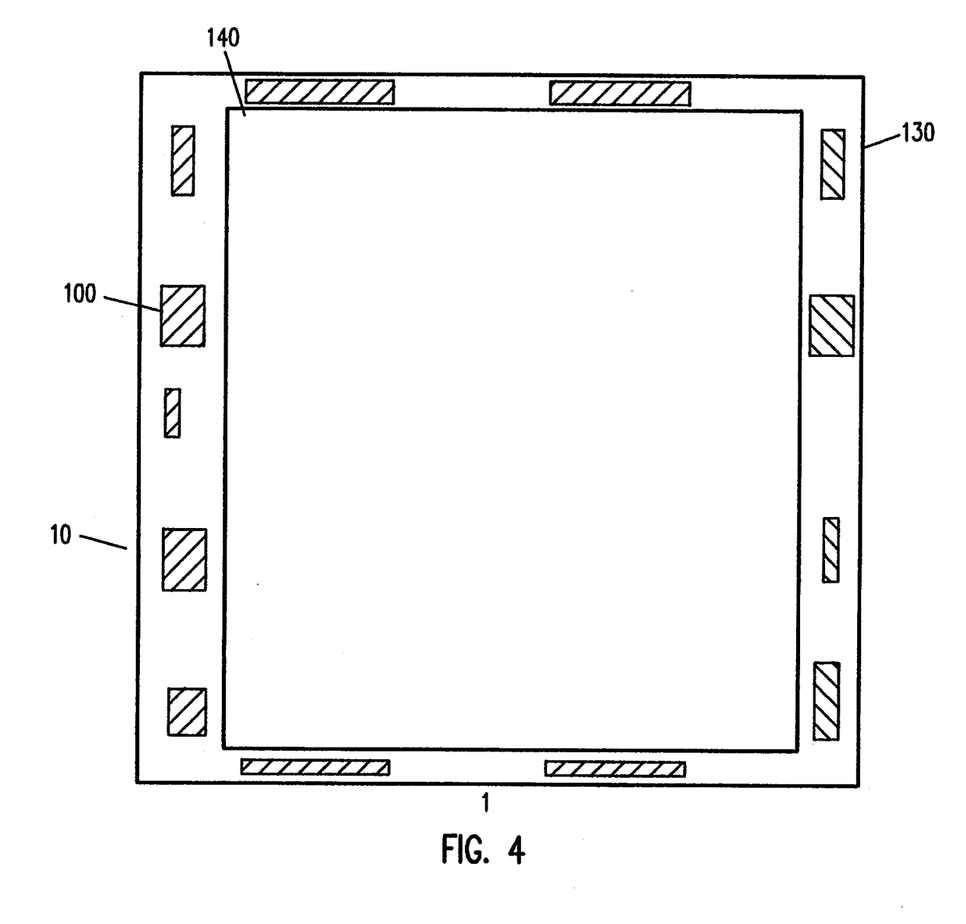
FIG. 4 is a top-view of a section of an unpatterned wafer of semiconductor material which will be used to fabricate a calibration wafer according to a second embodiment of the present invention, into which has been etched a minimal pattern of features by means of standard photolithographic techniques or other patterning method.

A second embodiment of the present invention consists of a calibration wafer having a pattern etched into the substrate itself. In this case, one starts with a substrate 10, typically silicon, and then applies a layer of resist. The resist is exposed, again by means of a photolithography mask and illumination source. The amount of patterned area produced by the mask is again chosen based on the previously discussed criteria.

After exposure, the resist is developed. Then wafer 10 is etched by etch means known in the semiconductor industry. The depth of the etched features should be such that the pattern of features is detectable by the scanner after the subsequent deposition of a film layer. FIG. 4 is a top-view of a die 15 on the wafer of semiconductor material 10 which is used to fabricate a calibration wafer 1 according to a second embodiment of the present invention, and into which has been etched a pattern of features 100 by means of standard photolithographic techniques. As mentioned when discussing the first embodiment of the present invention, the etching of the patterns onto the wafer serves to divide the top surface of die 15 into a center region 140 which is devoid of any pattern, and a peripheral region 130 within which a pattern of shapes 100 is defined and etched.

Figure 5:
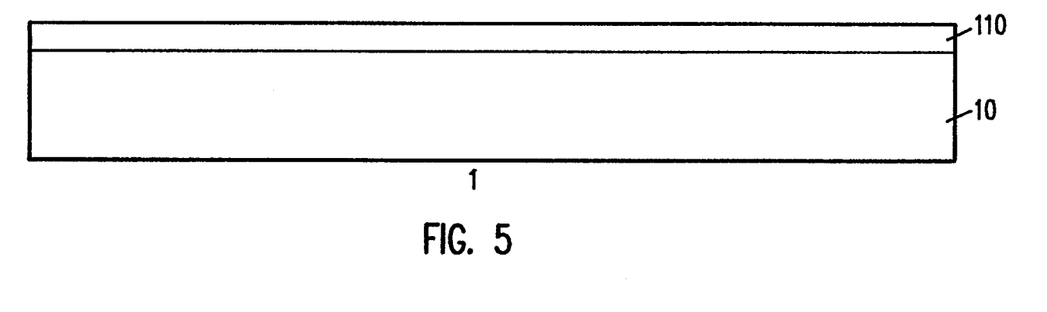
FIG. 5 is a cross-sectional view of the wafer of FIG. 4 after deposition of a layer of film.

After the etching step, the remaining resist is removed by chemical or dry methods known in the semiconductor industry. The calibration wafer 1 can then be cleaned, if desired, by chemical or mechanical methods. The next step is to deposit a layer or layers of film onto the top surface of wafer 1. As before, the layer(s) should be composed of materials typically used during the fabrication integrated circuits. FIG. 5 is a cross-sectional view of the calibration wafer 1 of FIG. 4 after deposition of a layer of film 110.

Figure 6:
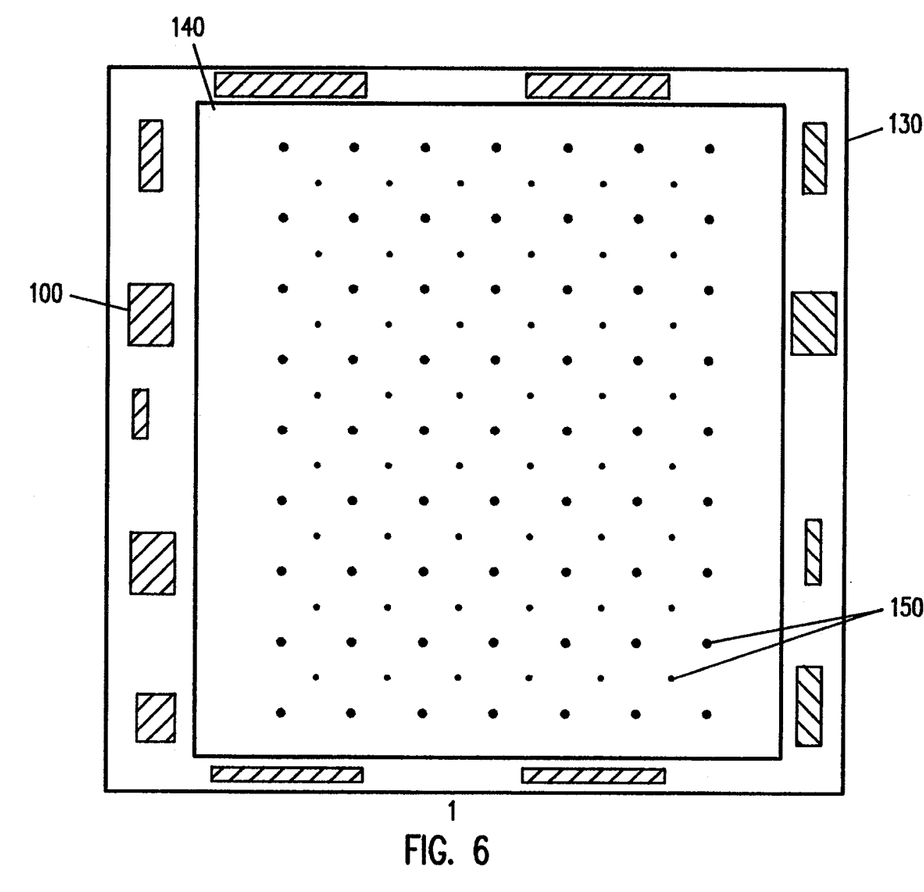
FIG. 6 is a top-view of the wafer of FIG. 5 onto which has been deposited a substantially uniform distribution of particles of a type or types typically deposited during the fabrication of a semiconductor device.

After deposition of the film layer(s), a substantially uniform distribution of particles is deposited. As before, the particles are of a size and material typically encountered during the fabrication of integrated circuits. The deposition should again be performed in a controlled environment to avoid contaminating the calibration wafer 1 with undesired materials. FIG. 6 is a top-view of a die 15 on the calibration wafer 1 of FIG. 5 after etching, and onto which has been deposited a substantially uniform distribution of particles 150 of a type or types typically deposited during the fabrication of a semiconductor device.

The calibration wafer 1 should then be tested against a primary calibration wafer (if one exists) for purposes of quality control. If desired, a set of calibration wafers 1 may be produced, each with a different film layer 110 and particle distribution 150. Each wafer so produced can be used to calibrate the scanner during a particular phase of a standard fabrication process. In this case, the type of film and type and number of particles deposited on the wafer depends on the stage of the fabrication process involved. The calibration wafer or wafers 1 should then be assembled and wrapped in a clean environment.

The calibration wafer of the present invention has several benefits over currently used means for calibrating patterned wafer scanners. The wafers have a sufficient pattern to allow patterned wafer scanners to focus and step across the wafer, but they also have sufficient open area in which the desired types and distribution of defects can be deposited.

Further, because the defects are based on film layers and the deposition of particles, a wider range of defect types and sizes can be simulated, as the resolution limits of photolithography techniques do not affect the defects which can be created on the wafer. And finally, because the wafers are fabricated so as to have a known distribution of defects, the calibration wafers can be used both to assess the repeatability of scan results and the sensitivity of the scanners.

It is noted that patterned wafer scanners used in conjunction with the calibration wafers of the present invention may also be used as a diagnostic tool for the detection and calibration of other materials or films which may be deposited onto a substrate. For example, the size and other pertinent characteristics of airborne particles deposited onto a wafer prepared in accordance with the steps outlined above can be determined by using a patterned wafer scanner. The benefit of using a patterned wafer scanner for such analysis is that the pattern can assist in locating the deposited particles after they are detected. The deposited particles may then be analyzed by other available methods such as Scanning Electron Microscopy, Auger Emission Spectroscopy, or Transmission Electron Microscopy. This technique may be useful in terms of tracking airborne pollutants.

A similar approach can be used to detect defects in film layers. In this situation, the calibration wafers of the present invention are prepared in accordance with the described technique, however, now no particles are deposited after deposition of the film layer(s). The defects detected by a scanner will then be those associated with the film layer or the deposition process.

Figure 7:
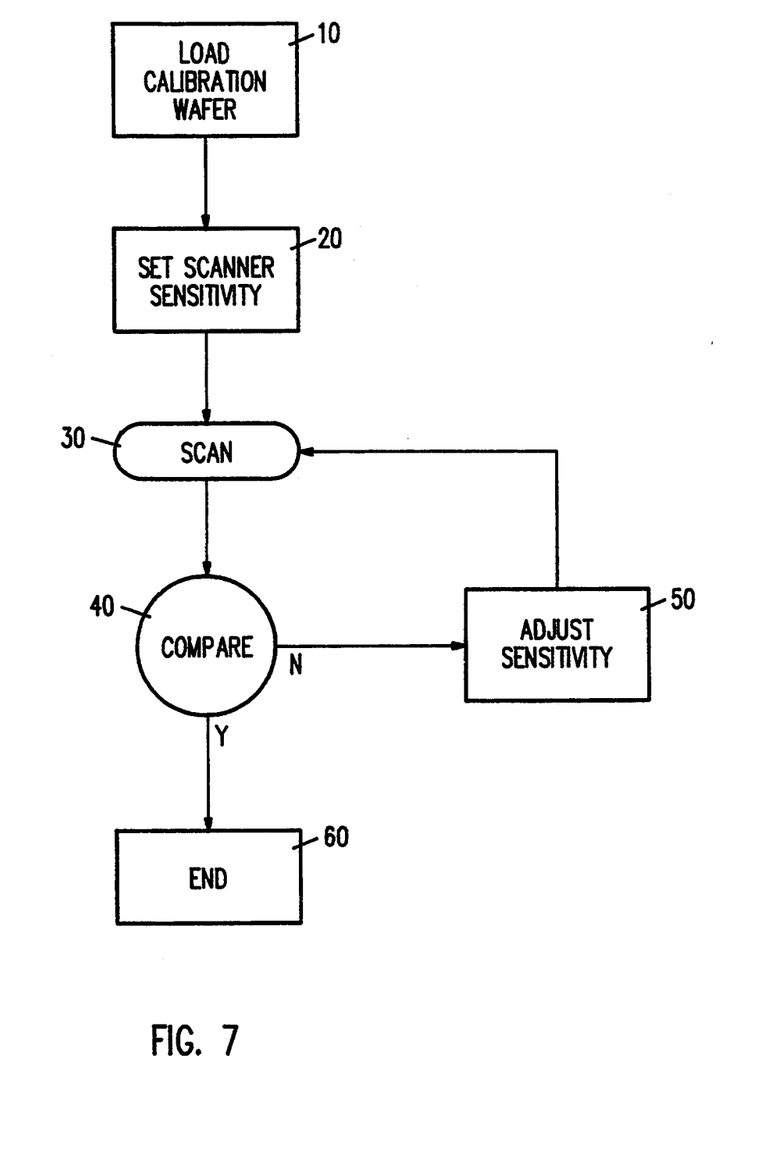
FIG. 7 is a flowchart which depicts the steps involved in the calibration of a patterned wafer scanner using a calibration wafer of the present invention.

The present invention is also directed to a method for calibrating patterned wafer scanners which is based on using a calibration wafer of the type disclosed in this application. FIG. 7 is a flowchart which depicts the steps involved in the calibration of a patterned wafer scanner using a calibration wafer of the present invention.

The first step of the method is to load an appropriate calibration wafer into the patterned wafer scanner, as indicated by step 10 in the figure. The calibration wafer chosen depends upon what stage of the fabrication process is the one for which the scanner is being calibrated. The wafer selected should be one whose materials and distribution of defects are typical of the those found in that particular stage of the fabrication process.

Next the scanner sensitivity is set, as indicated by step 20. The sensitivity should be set to the maximum value, if this is the first scan for the calibration wafer being scanned, or the sensitivity should be set to whatever value it was previously set to if the calibration wafer was previously scanned.

The calibration wafer is then scanned, as indicated by step 30. The scan detects a particular distribution of defects and types of defects on the calibration wafer. This data is then compared in step 40 to the distribution of defects and types of defects which are known to exist on the calibration wafer. If the results agree to a desired degree, then the scanner calibration process ends, as indicated by step 60. In this case the sensitivity setting on the scanner is left at its present setting and the scanner is calibrated.

If the results of the compare operation in 40 indicate that the scan data does not agree to a desired degree, then the sensitivity is adjusted in step 50 and a scan of the calibration wafer is performed again in step 30. The cycle of adjusting the sensitivity, scanning the wafer, and comparing the results continues until the scan data is sufficiently close to the known distribution of defects. In addition to, or instead of adjusting the sensitivity in step 50, the scanner can also be put through a diagnostic sequence to determine if it is operating properly.

While the present invention has been described with reference to the specific embodiment and elements disclosed, it is understood that other, equivalent embodiments of the invention are possible, and that the practice of the invention is not intended to be limited solely to the embodiments specifically disclosed in this application.

I claim:

1. A calibration wafer for use in calibrating patterned wafer scanners which focus onto a wafer, detect defects in the wafer, and step across regions of the wafer, where the scanner is used to detect defects in wafers of semiconductor material during the semiconductor device fabrication process, the calibration wafer comprising:

an unpatterned wafer having an interior region and a periphery region onto which has been deposited a layer of material, wherein such material is representative of a material which is deposited on a wafer during a step or steps performed during the fabrication process;

a pattern of features formed on the material layer and limited to the periphery region of the wafer, wherein such pattern covers sufficient area to permit the scanner to operate on the calibration wafer and to perform its stepping and focusing operations, and to detect known defects deposited on the calibration wafer with a desired degree of confidence; and a substantially uniform distribution of particles deposited onto the layer of material.

2. The calibration wafer of claim 1, wherein the layer of material deposited on the wafer is selected from the group consisting of silicon nitride, silicon oxide, polysilicon, aluminum or silicide.

3. The calibration wafer of claim 1, wherein the particles deposited onto the layer of material are selected from the group consisting of polystyrene latex, silicon, silicon nitride, silicon oxide, polysilicon, aluminum or silicide.

4. A calibration wafer for use in calibrating patterned wafer scanners which focus onto a wafer, detect defects in the wafer, and step across regions of the wafer, where the scanner is used to detect defects in wafers of semiconductor material during the semiconductor device fabrication process, the calibration wafer comprising:

an unpatterned wafer having an interior region and a periphery region onto which has been formed a pattern of features, the pattern of features being limited to the periphery region of the wafer, wherein such pattern covers sufficient area to permit the scanner to operate on the calibration wafer and to perform its stepping and focusing operations, and to detect known defects deposited on the calibration wafer with a desired degree of confidence;

a layer of material deposited on the surface of the wafer, wherein such material is representative of a material which is deposited on a wafer during a step or steps performed during the fabrication process; and a substantially uniform distribution of particles deposited onto the layer of material.

5. The calibration wafer of claim 4, wherein the layer of material deposited on the wafer is selected from the group consisting of silicon nitride, silicon oxide, polysilicon, aluminum or silicide.

6. The calibration wafer of claim 4, wherein the particles deposited onto the layer of material are selected from the group consisting of polystyrene latex, silicon, silicon nitride, silicon oxide, polysilicon, aluminum or silicide.

7. A method for calibrating a patterned wafer scanner which is used to detect defects in wafers of semiconductor material during the semiconductor device fabrication process, the method comprising:

(a) preparing a calibration wafer for the purpose of calibrating the scanner, wherein the preparation of the calibration wafer comprises:

depositing a layer of material onto an unpatterned wafer having an interior region and a periphery region, wherein such material is representative of a material which is deposited on a wafer during a step or steps performed during the fabrication process;

forming a pattern of features on the material layer and limited to the periphery region of the wafer, wherein such pattern covers sufficient area to permit the scanner to perform its stepping and focusing operations, and to detect known defects deposited on the calibration wafer with a desired degree of confidence; and depositing a substantially uniform distribution of particles onto the layer of material;

(b) arranging the calibration wafer in the scanner, wherein the scanner has an adjustable sensitivity, and further wherein the sensitivity of the scanner is adjusted to be the maximum scanning sensitivity;

(c) scanning the calibration wafer;

(d) comparing the results of the scan of the calibration wafer to a prior scan of the calibration wafer, wherein if the results of the scan performed in (c) differ from the prior scan of the calibration wafer, the sensitivity of the scanner is adjusted; and (e) repeating, if necessary, steps (c) and (d) until the results of the latest scan are substantially the same as the prior scan.

8. The method of claim 7, wherein the preparation of the calibration wafer comprises:

forming a pattern of features on an unpatterned wafer having an interior region and a periphery region with the pattern of features being limited to the periphery region of the wafer, wherein such pattern covers sufficient area to permit the scanner to perform its stepping and focusing operations, and to detect known defects deposited on the calibration wafer with a desired degree of confidence;

depositing a layer of material on the surface of the wafer, wherein such material is representative of a material which is deposited on a wafer during a step or steps performed during the fabrication process; and depositing a substantially uniform distribution of particles onto the layer of material.

9. A method of detecting defects in material layers deposited onto a wafer of semiconductor material using a patterned wafer scanner which focuses onto a wafer, detects defects in the wafer, and steps across regions of the wafer, the method comprising:

preparing a test wafer which will be scanned by the scanner to detect defects associated with the deposited material layer and a deposition process used to deposit the material layer, wherein the preparation of the test wafer comprises:

depositing a layer of material onto an unpatterned wafer having an interior region and a periphery region, wherein such material is representative of a material which is deposited onto a wafer during a step or steps performed during the fabrication of semiconductor devices; and forming a pattern of features on the material layer and limited to the periphery region of the wafer, wherein such pattern covers sufficient area to permit the scanner to operate on the test wafer and to perform its stepping and focusing operations, and to detect defects in the material layer with a desired degree of confidence; and scanning the test wafer with the patterned wafer scanner so as to detect any defects associated with the deposited material layer and the deposition process.

10. The method of claim 9, wherein the preparation of the test wafer comprises:

forming a pattern of features on an unpatterned wafer having an interior region and a periphery region with the pattern of features being limited to the periphery of the wafer, wherein such pattern covers sufficient area to permit the scanner to perform its stepping and focusing operations, and to detect defects in the material layer with a desired degree of confidence; and depositing a layer of material on the surface of the wafer, wherein such material is representative of a material which is deposited on a wafer during a step or steps performed during the fabrication of semiconductor devices.

11. A method of detecting airborne particles deposited onto a substrate using a patterned wafer scanner which focuses onto a wafer, detects defects in the wafer, and steps across regions of the wafer, the method comprising:

preparing a substrate having an interior region and a periphery region which will be used to detect airborne particles which are deposited onto the substrate, wherein the preparation of the substrate comprises;

depositing a layer of material onto the substrate, wherein such material is representative of a material which is deposited on an unpatterned wafer during the fabrication of a semiconductor device; and forming a pattern of features on the material layer which is limited to the periphery region of the wafer, wherein such pattern covers sufficient area to permit the scanner to perform its stepping and focusing operations, and to permit the scanner to detect airborne particles deposited on the substrate with a desired degree of confidence;

depositing airborne particles onto the substrate; and scanning the substrate with the patterned wafer scanner to detect airborne particles deposited onto the substrate.

12. The method of claim 11 wherein the preparation of the substrate comprises:

forming a pattern of features on the substrate which is limited to the periphery region of the wafer, wherein such pattern covers sufficient area to permit the scanner to perform its stepping and focusing operations, and to detect airborne particles deposited on the substrate with a desired degree of confidence; and depositing a layer of material on the surface of the substrate, wherein such material is representative of a material which is deposited on an unpatterned wafer during the fabrication of a semiconductor device.

* * * * *